United States Patent [19]

Ishii et al.

[11] 4,382,953

[45] May 10, 1983

[54] OPHTHALMIC SOLUTION FOR INTRAOCULAR PRESSURE REDUCTION

[75] Inventors: Yukihisa Ishii; Yasuo Sakai; Takao Goto, all of Kusatsu; Kiyoshi Masuda, Otsu, all of Japan

[73] Assignee: Kakenyaku Kako Co., Ltd., Tokyo, Japan

[21] Appl. No.: 183,756

[22] Filed: Sep. 3, 1980

[30] Foreign Application Priority Data

Sep. 6, 1979 [JP] Japan ................................. 54-114820
Jul. 5, 1980 [JP] Japan ................................. 55-92067
Jul. 22, 1980 [JP] Japan ................................. 55-100947

[51] Int. Cl.$^3$ ............................................ A61K 31/34
[52] U.S. Cl. ................................................. 424/285
[58] Field of Search ........................................ 424/285

[56] References Cited

U.S. PATENT DOCUMENTS

| | | | |
|---|---|---|---|
| 4,056,626 | 11/1977 | Ito et al. | 424/285 |
| 4,127,674 | 11/1978 | Leopold | 424/324 |
| 4,189,496 | 2/1980 | Cragoe et al. | 424/285 |
| 4,229,467 | 10/1980 | Parker | 424/285 |
| 4,237,130 | 12/1980 | Cragoe et al. | 424/285 |

OTHER PUBLICATIONS

Brit J. Ophthal., (1973) pp. 301–303–Bonomi et al.
Chem. Abst. 77, 775(w) (1972)–Pecori–Giraldi.
Chem. Abst. 81, 131,068(y) (1974)–Stankiewicz et al.
Chem. Abst. 82, 38754(e) (1975)–Sharaf et al.

*Primary Examiner*—Douglas W. Robinson
*Attorney, Agent, or Firm*—Armstrong, Nikaido, Marmelstein & Kubovcik

[57] ABSTRACT

An ophthalmic solution suitable for adjusting intraocular pressure comprising (A) an ophthalmologically acceptable, water-soluble salt of 2-acetyl-7-(2-hydroxy-3-isopropylaminopropoxy)benzofuran, (B) benzalkonium chloride or benzethonium chloride, and (C) a member selected from polyvinyl alcohol, methyl cellulose, carboxymethyl cellulose, hydroxyethyl cellulose and hydroxypropylmethyl cellulose, the solution being adjusted to pH 5.0 to 8.0 with a buffer agent. The components (B) and (C) increase greately the intraocular penetration of the component (A) and reduce the irritation to eye of the component (A) so that the pharmacological action of the component (A) can be effectively exhibited. The ophthalmic solution produces an excellent effect on decreasing of intraocular pressure with reduced irritation to eye and stability for a long term.

11 Claims, 5 Drawing Figures

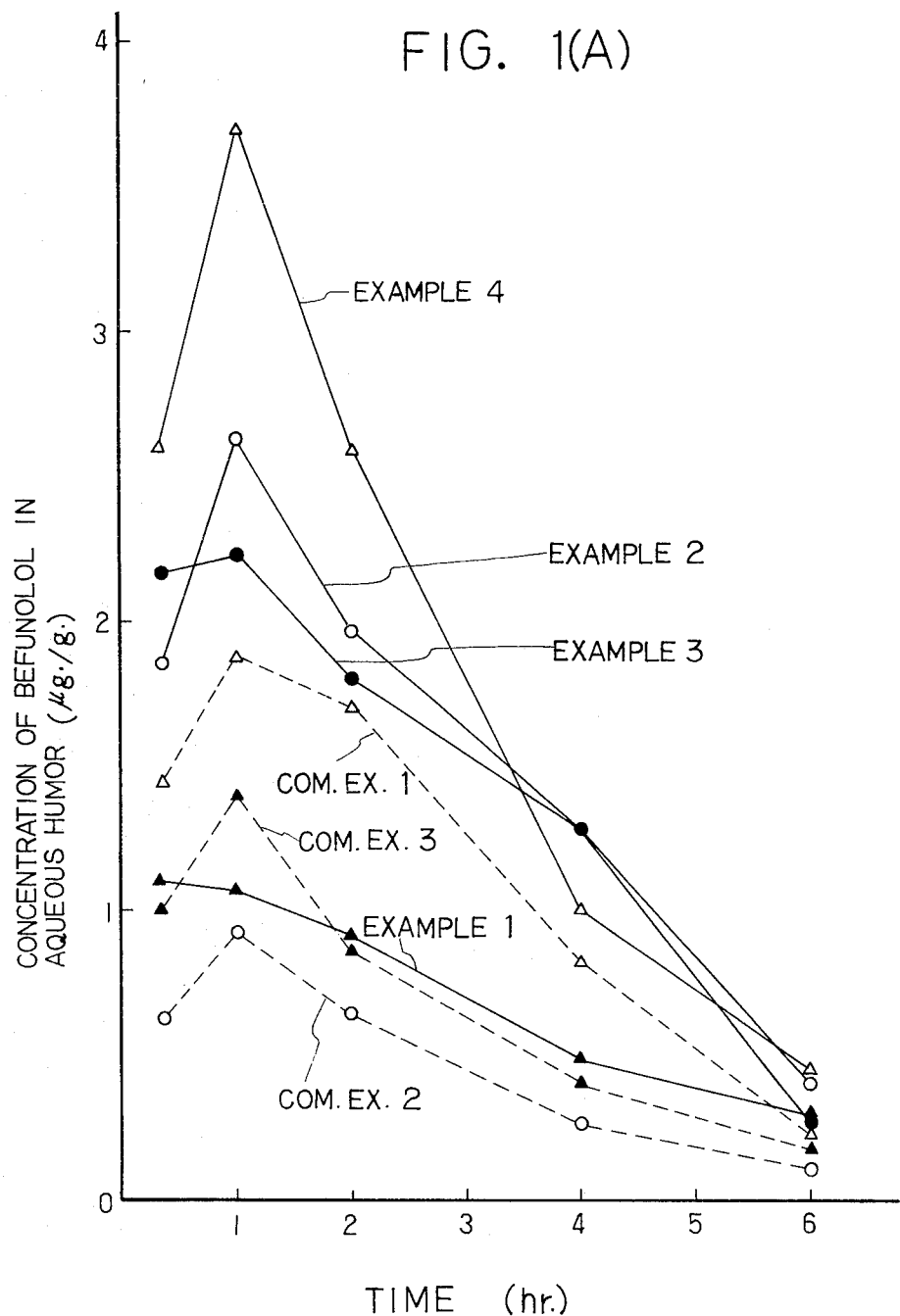

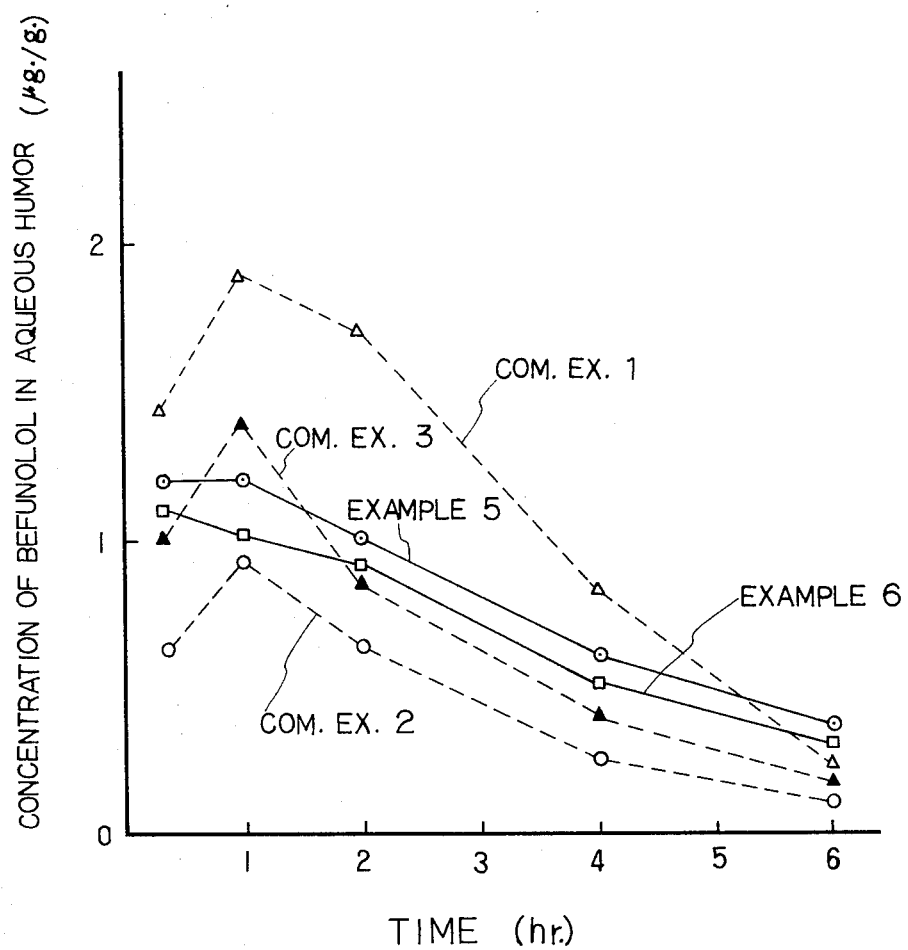

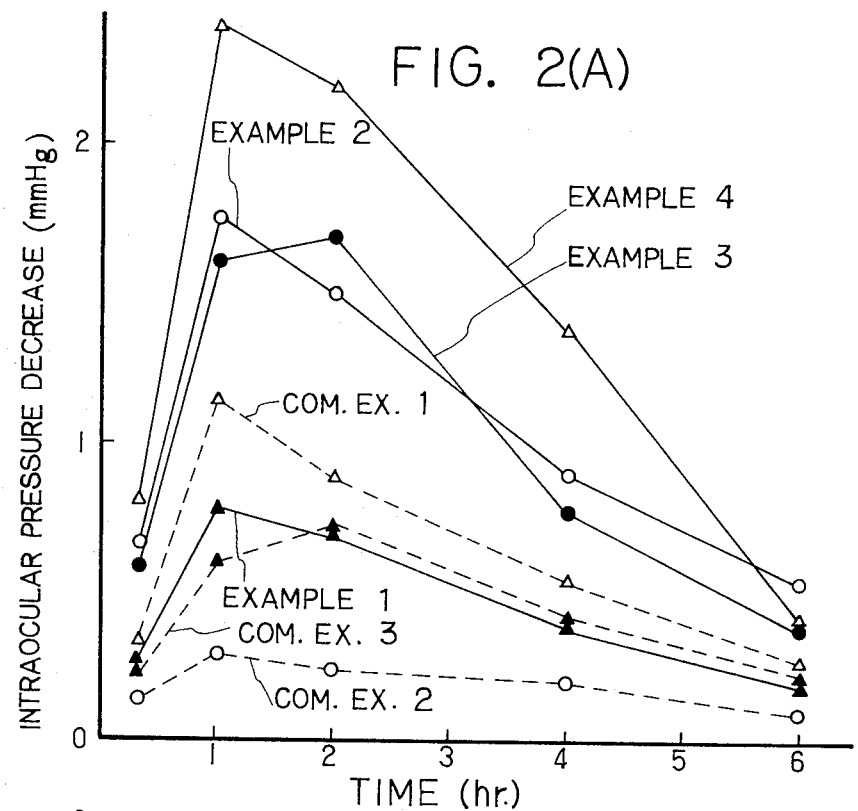
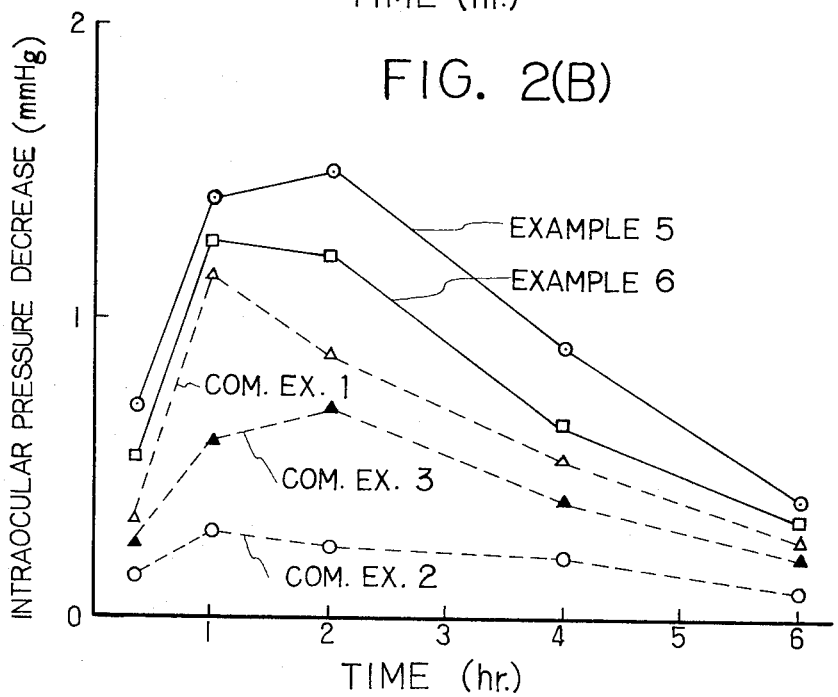

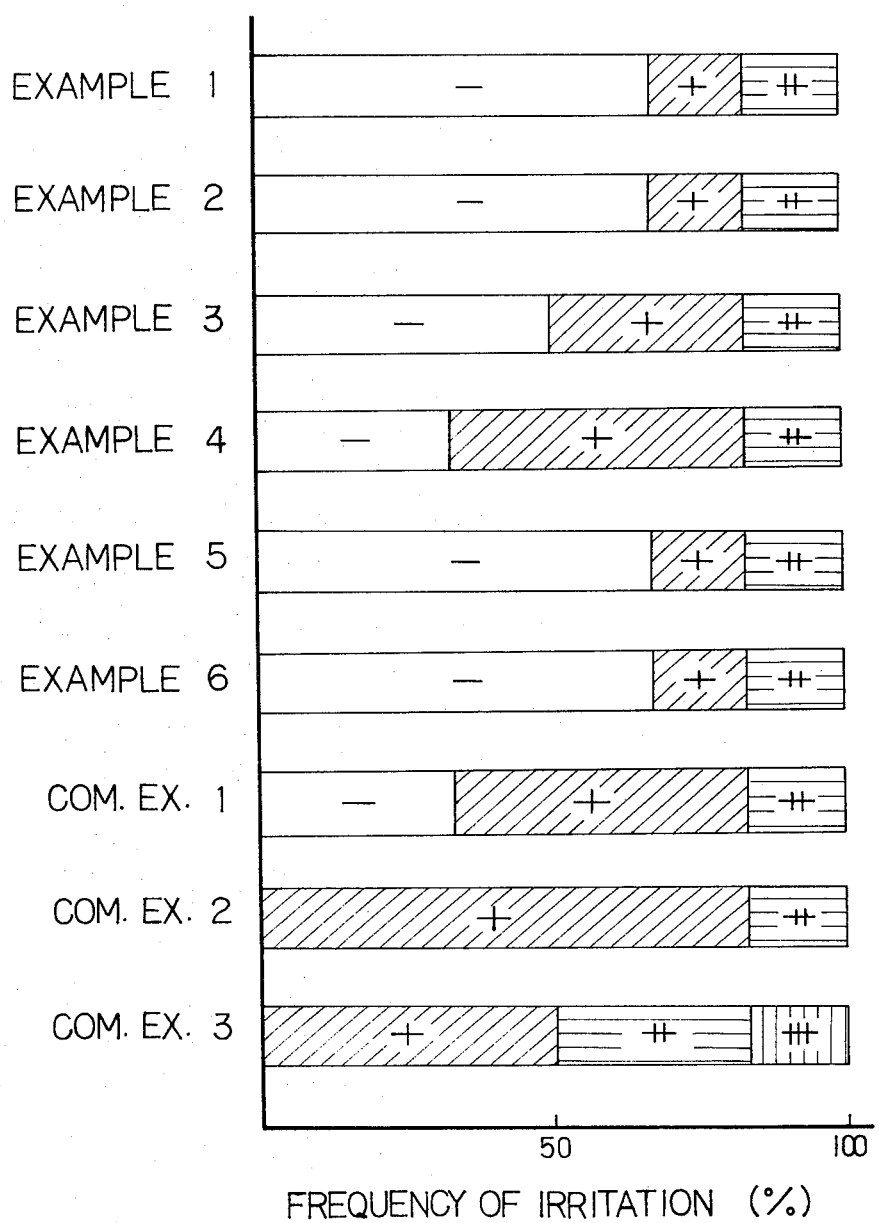

OPHTHALMIC SOLUTION FOR INTRAOCULAR PRESSURE REDUCTION

BACKGROUND OF THE INVENTION

The present invention relates to a novel ophthalmic solution for intraocular pressure adjustment, and more particularly to an ophthalmic solution for intraocular pressure adjustment useful for treatment of ocular hypertension and glaucoma.

Hitherto, a pilocarpine ophthalmic solution has been employed as agents for adjusting intraocular pressure for use in ocular hypertension and glaucoma. It is known that the pilocarpine ophthalmic solution decreases the intraocular pressure, but acts on sphincter of pupil and ciliary body and has side effects such as visual darkness due to miosis, disorder of accommodation and conjunctival injection. Such side effects bring about a serious danger particularly in working of persons who engage in communication and transportation undertakings. Also, in case of a middle-aged cataract patient, the side effects increase visual disorder due to miosis. From viewpoint of these defects, there has been desired development of intraocular pressure adjusting agents for ocular hypertension and glaucoma to be replaced by the pilocarpine ophthalmic solution.

An epinephrine ophthalmic solution was developed on the basis of such a demand, but has a side effect such as conjunctival injection, pain in eye-brow portion or allergic blepharoconjunctivitis and in some cases, brings about intraocular pressure rise due to mydriasis. Therefore, the epinephrine ophthalmic solution is not much employed. Also, it has been attempted clinically to use surface anesthetics and psychotropic drugs as drugs which produce decrease of intraocular pressure of glaucoma eye, but any drugs have not been put to practical use.

In recent years, β-blocking agents are watched in this region, and it was found that 2-acetyl-7-(2-hydroxy-3-isopropylaminopropoxy)benzofuran (hereinafter referred to as "befunolol") which is one of β-blocking agents and is increasing in its estimation as a cardiovascular agent, is also useful as an ophthalmic agent for treating ocular hypertension and glaucoma.

Fundamental properties required for pharmaceuticals are effectiveness, safety and stability. Therefore, in case of an ophthalmic solution for the treatment of ocular hypertension and glaucoma, the ophthalmic solution is required to have an effect of decreasing intraocular pressure and a proper durability of the effect, and moreover to have no side effects, that is, to have no effect on accommodation mechanism of pupil and refraction and to give no irritation, and also to be stable as preparations. Estimating the above-mentioned befunolol ophthalmic solution from these points of view, it is not yet a complete ophthalmic solution, though its effectiveness and safety are substantiated to some extent by Tane et al as reported in Japanese Review of Clinical Ophthalmology, Vol. 73, No. 3, 35–40 (1979).

It is an object of the present invention to provide an ophthalmic solution of befunolol which can be used safely with large effect and stability.

A further object of the invention is to provide an ophthalmic solution for intraocular pressure adjustment, which can exhibit the effects in a lower concentration of the effective component with reduced local irritation and is stable for a long term.

These and other objects of the invention will become apparent from the description hereinafter.

BRIEF DESCRIPTION OF THE DRAWINGS

FIGS. 1(A) and 1(B) are graphs showing change of befunolol concentration in the aqueous humor with the lapse of time after topical instillation of befunolol ophthalmic solutions of the invention to rabbit eyes;

FIGS. 2(A) and 2(B) are graphs showing intraocular pressure change with the lapse of time after topical instillation of befunolol ophthalmic solutions of the invention to rabbit eyes; and FIG. 3 is a graph showing frequency of irritation upon topical instillation of befunolol ophthalmic solutions of the invention to human eyes.

SUMMARY OF THE INVENTION

The present inventors have found the facts that the effect of befunolol on decrease of intraocular pressure depends on intraocular penetration of befunolol and the intraocular penetration can be remarkably increased by the presence of benzalkonium chloride or benzethonium chloride which serves as a preservative and by the presence of polyvinyl alcohol, methyl cellulose, carboxymethyl cellulose, hydroxyethyl cellulose or hydroxypropylmethyl cellulose which serves as a viscosity inducing agent, and that the intraocular penetration of befunolol can also be increased in a particular pH range, and that in the presence of the above-mentioned particular preservative and viscosity inducing agent in the particular pH range, the irritation of befunolol to human eye can be decreased and also befunolol is stable for a long term.

In accordance with the present invention, there is provided an ophthalmic solution for the adjustment of intraocular pressure comprising (A) 0.025 to 4.0 w/v % of an ophthalmologically acceptable, water-soluble salt of 2-acetyl-7-(2-hydroxy-3-isopropylaminopropoxy)-benzofuran, (B) 0.001 to 0.1 w/v % of benzalkonium chloride or benzethonium chloride, and (C) 0.01 to 2.0 w/v % of at least one member selected from the group consisting of polyvinyl alcohol, methyl cellulose, carboxymethyl cellulose, hydroxyethyl cellulose and hydroxypropylmethyl cellulose, the solution being adjusted to pH 5.0 to 8.0 with a buffer agent.

The ophthalmic solution of the present invention can effectively exhibit excellent pharmacological actions of befunolol, that is to say, the solution of the invention exerts the effect of decreasing the intraocular pressure, for instance, of glaucoma eye even at a low concentration of befunolol without side effects such as local irritation and is stable for a long term.

DETAILED DESCRIPTION

Befunolol [i.e. 2-acetyl-7-(2-hydroxy-3-isopropylaminopropoxy)benzofuran] is employed in the form of an ophthalmologically acceptable, water-soluble salt. Examples of the ophthalmologically acceptable, water-soluble salt of befunolol employed as a component (A) in the present invention are hydrochloric acid salt, citric acid salt, sulfuric acid salt, phosphoric acid salt, maleic acid salt and fumaric acid salt. The hydrochloric acid salt of befunolol, i.e. 2-acetyl-7-(2-hydroxy-3-isopropylaminopropoxy)benzofuran hydrochloride, is particularly preferred from viewpoints of economy and stability of the prepared ophthalmic solution. The befunolol may be in the dl-form or l-form. When the salt of l-befunolol is employed in combination with components (B) and (C), the excellent pharmacological actions of befunolol can be more effectively exhibited.

The concentration of the component (A) in the ophthalmic solution is selected from 0.025 to 4.0 w/v %. When the befunolol is a racemic compound, it is desirable to employ the component (A) in a concentration of at least 0.05 w/v % and the concentration is selected from 0.05 to 4.0 w/v %, preferably 0.1 to 2.0 w/v %. When the salt of l-befunolol is employed as a component (A), the use in a concentration of about half the concentration of dl-befunolol is sufficient, and the concentration is selected from 0.025 to 2.0 w/v %, preferably 0.05 to 1.0 w/v %. When the concentration of the component (A) is less than the above range, the effect of decreasing intraocular pressure is not remarkable. On the other hand, the use of the component (A) in a concentration of more than the above range is not only uneconomical, but also provides an ophthalmic solution undesirable as a drug for treating glaucoma because of occurrence of local anesthesia action.

Benzalkonium chloride and benzethonium chloride are employed as a component (B) in the present invention, and they may be employed alone or in admixture thereof. The component (B) employed in the invention accelerates the permeability of the component (A) through the cornea so as to increase the amount of the component (A) penetrated into the eye in cooperation with the component (B), while it serves as a usual preservative for preventing contamination with bacteria and the like. It cannot be expected to increase the intraocular penetration of the component (A) by the use of a preservative such as methyl p-hydroxybenzoate or propyl p-hydroxybenzoate. Benzalkonium chloride is particularly preferred, since it exhibits the antiseptic effect in a low concentration and is effective to Pseudomonas aeruginosa and is also low in irritation to mucous membrane of the eye. The concentration of the component (B) in the ophthalmic solution is selected from 0.001 to 0.1 w/v %, preferably 0.003 to 0.01 w/v %. When the concentration of the component (B) is less than the above range, the antiseptic effect is not sufficient and also the intraocular penetration of the component (A) is not sufficiently increased. On the other hand, the use of the component (B) in concentrations of more than the above range reveals undesirable actions such as local irritation.

The component (C) employed in the invention accelerates the permeability of the component (A) into the cornea so as to increase the intraocular penetration of the component (A) in cooperation with the component (B), while it serves as a viscosity inducing agent to provide the resulting ophthalmic solution with viscosity so as to make the effect of decreasing intraocular pressure sustain or to protect the cornea. Examples of the component (C) employed in the present invention are polyvinyl alcohol, methyl cellulose, carboxymethyl cellulose, hydroxyethyl cellulose and hydroxypropylmelthyl cellulose. These compounds may be employed alone or in admixture thereof. Polyvinyl alcohol is preferred by the reasons that polyvinyl alcohol having a uniform quality is easily obtainable and also the solubility in water is good. Hydroxypropylmethyl cellulose is also preferred, since the synergistic effects obtained by using the component (A) in combination with the components (B) and (C) are great, that is to say, by the reasons that the intraocular penetration of the component (A) is more remarkably increased and the irritation to the human eye by the component (A) is more remarkably decreased and moreover the component (A) is stable for a longer term. The concentration of the component (C) is selected from 0.01 to 2.0 w/v %, preferably 0.02 to 1.5 w/v %. In case of employing the compounds other than hydroxypropylmethyl cellulose, it is desirable to employ them in a concentration of at least 0.02 w/v %, especially 1.0 to 1.5 w/v %. In case of employing hydroxypropylmethyl cellulose, a lower concentration is sufficient and it is desirably employed in a concentration of 0.01 to 1.0 w/v %, especially 0.1 to 0.5 w/v %. When the concentration of the component (C) is less than 0.01 w/v %, the effect of sustaining the intraocular pressure decreasing action, the effect of protecting the cornea and the effect of increasing the intraocular penetration of the component (A) are poor. Also, when the concentration of the component (C) is more than 2.0 w/v %, not only the preparation becomes difficult due to increase of the viscosity, but also the resulting ophthalmic solution gives an uncomfortable sensation upon instillation.

The ophthalmic solution of the present invention is adjusted to pH 5.0 to 8.0, preferably pH 6.8 to 7.6. The penetration of the component (A) into the eye is increased in such a pH range. Moreover, this pH range is almost in accord with the pH range of tear and the use of the components (B) and (C) coupled with this pH range decreases the irritation action of the component (A). When the pH of the solution is higher than the above range, the solubility of the component (A) in water is lowered, and when the pH is lower than the above range, the amount of intraocular penetration of the component (A) is decreased. Any buffer agents which are ophthalmologically acceptable are usable in the present invention to adjust the pH of the ophthalmic solution. For instance, a combination of potassium dihydrogenphosphate and disodium hydrogenphosphate is mentioned as a preferably buffer agent.

The ophthalmic solution of the present invention may contain usual additives such as sodium chloride, potassium chloride and boric acid.

The ophthalmic solution of the present invention has an excellent effect on the decrease of intraocular pressure such that the intraocular pressure of a ocular hypertension glaucoma patient becomes normal in about 3 to about 4 hours after instillation of 1 or 2 drops of the ophthalmic solution of the invention.

A process for preparing the ophthalmic solution of the present invention is not limited to a specific one, and a usual process is adoptable. For instance, the component (C) is dissolved in an aqueous solution of a buffer agent, and the components (A) and (B) are then added to and dissolved in the solution. After adjusting to a desired concentration by adding water to the resulting solution, the solution is filtered to sterilize. Water used as a medium is usually a sterile purified water.

The ophthalmic solution of the present invention is more particularly described and explained by means of the following Examples.

EXAMPLES 1 to 6 AND COMPARATIVE EXAMPLES 1 to 3

Ophthalmic solutions were prepared according to prescriptions shown in Table 1 by dissolving sodium chloride in 80 ml. of a solution of pH 5.0 to 8.0 prepared by dissolution of a buffer agent (anhydrous potassium dihydrogenphosphate and disodium hydrogenphosphate dodecahydrate) in sterile purified water, dissolving the component (C) (polyvinyl alcohol or hydroxypropylmethyl cellulose) in the solution with vigorous agitation, then adding and dissolving the component (A) (befunolol hydrochloride) and a 10% by weight aqueous solution of the component (B) (benzalkonium chloride) into the solution, and after adding sterile purified water to the solution to adjust the total volume to 100 ml., sterilizing through a filter.

Ophthalmic solution of Comparative Examples 1 to 3 were prepared by dissolving sodium chloride in 80 ml. of the phosphate buffer solution, then adding the component (A) and a 10% by weight aqueous solution of the component (B) (Comparative Example 1) or methyl p-hydroxybenzoate and propyl p-hydroxybenzoate as a preservative (Comparative Examples 2 and 3) into the solution and dissolving at about 60° C., adding sterile purified water to the solution to adjust the total volume to 100 ml., and sterilizing through a filter.

TABLE 1

| | Ex. 1 | Ex. 2 | Ex. 3 | Ex. 4 | Ex. 5 | Ex. 6 | Com. Ex. 1 | Com. Ex. 2 | Com. Ex. 3 |
|---|---|---|---|---|---|---|---|---|---|
| Components (g.) | | | | | | | | | |
| dl-Befunolol.HCl | 0.25 | 0.5 | 0.5 | 1.0 | — | — | 0.5 | 0.5 | 1.0 |
| l-Befunolol.HCl | — | — | — | — | 0.25 | 0.25 | — | — | — |
| $KH_2PO_4$ (anhydrous) | 0.250 | 0.250 | 0.250 | 0.250 | 0.250 | 0.250 | 0.250 | 0.303 | 0.303 |
| $Na_2HPO_4.12H_2O$ | 2.859 | 2.859 | 2.859 | 2.859 | 2.859 | 2.859 | 2.859 | 0.794 | 0.794 |
| Sodium chloride | 0.103 | 0.069 | 0.069 | — | 0.095 | 0.095 | 0.069 | 0.489 | 0.411 |
| Hydroxypropylmethyl cellulose | — | 0.5 | — | 0.5 | 0.5 | — | — | — | — |
| Polyvinyl alcohol | 1.5 | — | 1.5 | — | — | 1.5 | — | — | — |
| 10% Aqueous solution of benzalkonium chloride (ml.) | 0.08 | 0.08 | 0.08 | 0.08 | 0.08 | 0.08 | 0.08 | — | — |
| Methyl p-hydroxybenzoate | — | — | — | — | — | — | — | 0.036 | 0.036 |
| Propyl p-hydroxybenzoate | — | — | — | — | — | — | — | 0.019 | 0.019 |
| Total volume (ml.) | 100 | 100 | 100 | 100 | 100 | 100 | 100 | 100 | 100 |
| pH | 7.4 | 7.4 | 7.4 | 7.4 | 7.4 | 7.4 | 7.4 | 6.7 | 6.7 |

The ophthalmic solutions prepared according to the present invention were placed in light-shielding vessels and stored in a sunlight box (40° to 50° C., more than 6,000 luxes every other day). No change was observed even after one month.

The obtained ophthalmic solutions were then subjected to the following tests.

(1) Intraocular penetration of befunolol

To each of the eyes of a group of 3 rabbits not anesthetized was instilled 20 μl. of the befunolol ophthalmic solution, and after 20 minutes, the aqueous humor was taken out by a syringe and the concentration of befunolol in the aqueous humor was measured. This procedure was repeated except that the concentration of befunolol was measured after 1, 2, 4 and 6 hours from the topical instillation of the befunolol ophthalmic solution.

The results are shown in FIGS. 1(A) and 1(B) wherein each point represents the mean value of three rabbits, the vertical scale represents the concentration of befunolol in the aqueous humor (μg./g.) and the horizontal scale represents the time after instillation (hour).

(2) Decrease of intraocular pressure

The intraocular pressure was measured by a tonometer with the lapse of time after instillation of the befunolol ophthalmic solution to the rabbit eyes, and there was then obtained the difference in the intraocular pressure between before and after treatment with the befunolol solution.

The results are shown in FIGS. 2(A) and 2(B) wherein each point represents the mean value of three rabbits, the vertical scale represents the intraocular pressure decrease (mmHg) and the horizontal scale represents the time after instillation (hour).

(3) Irritation to the human eye

A drop (about 35 μl.) of the befunolol ophthalmic solution was instilled to each of 6 volunteers of normal adult men 22 to 39 years old, and the degree of irritation was observed and estimated according to the following criteria.

(−): No irritation
(+): Slight irritation
(++): Clear irritation
(+++): Strong irritation The results are shown in FIG. 3 wherein the horizontal scale represents the frequency of irritation (%).

FIGS. 1(A), 1(B), 2(A), 2(B) and 3 clearly show that the intraocular penetration and action of decreasing intraocular pressure of the befunolol can be increased by the presence of the component (B), e.g. benzalkonium chloride, and the component (C), e.g. polyvinyl alcohol or hydroxypropylmethyl cellulose, and also the irritation of the befunolol to the human eye can be decreased by the presence of the components (B) and (C).

EXAMPLE 7

Ophthalmic solutions were prepared according to the prescription of Example 2 except that the amounts of anhydrous potassium dihydrogenphosphate and disodium hydrogenphosphate dodecahydrate were changed to adjust pH of the solution as shown in Table 2. With respect to the obtained ophthalmic solutions, there was measured the concentration of befunolol in the aqueous humor after 1 hour from the instillation of the solution to observe the intraocular penetration of befunolol according to the procedure in the preceding Examples.

The results are shown in Table 2.

In the same manner as above, ophthalmic solutions were prepared according to the prescription of Example 3 to give the solutions of various pH as shown in Table 3 and according to the prescription of Example 5 to give the solutions of various pH as shown in Table 4, and the intraocular penetration of befunolol after 1 hour from the instillation was measured. The results are shown in Tables 3 and 4, respectively.

In case of the ophthalmic solutions of pH 8.5, the preparation was impossible due to occurrence of precipitation.

TABLE 2

| pH | 4.5 | 5.4 | 6.7 | 7.6 | 8.5 |
|---|---|---|---|---|---|
| Concentration of befunolol in | 0.3 | 0.9 | 2.0 | 2.6 | — |

TABLE 2-continued

| pH | 4.5 | 5.4 | 6.7 | 7.6 | 8.5 |
|---|---|---|---|---|---|
| aqueous humor (μg./g.) | | | | | |

TABLE 3

| pH | 4.5 | 5.4 | 6.7 | 7.6 | 8.5 |
|---|---|---|---|---|---|
| Concentration of befunolol in aqueous humor (μg./g.) | 0.3 | 0.7 | 1.7 | 2.4 | — |

TABLE 4

| pH | 4.5 | 5.4 | 6.7 | 7.6 | 8.5 |
|---|---|---|---|---|---|
| Concentration of befunolol in aqueous humor (μg./g.) | 0.1 | 0.4 | 0.9 | 1.3 | — |

From Tables 2 to 4, it is observed that the intraocular penetration of befunolol increases with the rise of pH and a sufficient intraocular penetration is obtained in the range of pH 5.0 to 8.0, and that the intraocular penetration of befunolol is insufficient when the pH of the ophthalmic solution is lower than 5.0, and further that the preparation of ophthalmic solution is impossible when the pH of the solution is higher than 8.0.

EXAMPLE 8

Ophthalmic solutions of pH 7.4 were prepared according to the prescription of Example 2 except that the concentration of benzalkonium chloride was variously changed as shown in Table 5. With respect to the obtained ophthalmic solutions, there was measured the concentration of befunolol in the aqueous humor after 20 minutes from the instillation of the solution to observe the intraocular penetration of befunolol according to the procedure in Examples 1 to 6.

The results are shown in Table 5.

The above procedure was repeated except that ophthalmic solutions were prepared according to the prescription of Example 3 to give the solutions containing benzalkonium chloride in various concentrations as shown in Table 6 and according to the prescription of Example 5 to give the solutions containing benzalkonium chloride in various concentrations as shown in Table 7. The results are shown in Tables 6 and 7, respectively.

TABLE 5

| Concentration of benzalkonium chloride (w/v %) | 0 | 0.0005 | 0.0015 | 0.004 | 0.009 | 0.02 | 0.08 | 0.12 |
|---|---|---|---|---|---|---|---|---|
| Concentration of befunolol in aqueous humor (μg./g.) | 0.8 | 0.9 | 1.5 | 1.8 | 2.6 | 2.8 | 2.7 | 2.6 |

TABLE 6

| Concentration of benzalkonium chloride (w/v %) | 0 | 0.0005 | 0.0015 | 0.004 | 0.009 | 0.02 | 0.08 | 0.12 |
|---|---|---|---|---|---|---|---|---|
| Concentration of befunolol in aqueous humor (μg./g.) | 0.8 | 0.9 | 1.2 | 1.8 | 2.2 | 2.5 | 2.6 | 2.6 |

TABLE 7

| Concentration of benzalkonium chloride (w/v %) | 0 | 0.0005 | 0.0015 | 0.004 | 0.009 | 0.02 | 0.08 | 0.12 |
|---|---|---|---|---|---|---|---|---|
| Concentration of befunolol in aqueous humor (μg./g.) | 0.4 | 0.5 | 0.6 | 1.0 | 1.2 | 1.1 | 1.3 | 1.4 |

From Tables 5 to 7, it is observed that the intraocular penetration of befunolol increases with the increase of the benzalkonium chloride concentration and a sufficient intraocular penetration is obtained in the concentration of benzalkonium chloride within the range of 0.001 to 0.1 w/v %, and that when the concentration of benzalkonium chloride is less than 0.001 w/v %, the intraocular penetration of befunolol is insufficient, and that when the concentration of benzalkonium chloride is more than 0.1 w/v %, the intraocular penetration of befunolol does not increases with the increase of the concentration and moreover the irritation to the mucous membrane of the eye becomes strong too much.

EXAMPLES 9 to 26

Ophthalmic solutions were prepared according to prescriptions shown in Table 8 in the same manner as in Examples 1 to 6.

The obtained ophthalmic solutions showed an excellent action of decreasing intraocular pressure with a decreased irritation to the eye and were also stable for a long term.

TABLE 8

| | Ex. 9 | Ex. 10 | Ex. 11 | Ex. 12 | Ex. 13 | Ex. 14 |
|---|---|---|---|---|---|---|
| Components (g.) | | | | | | |
| dl-Befunolol.HCl | 0.125 | 0.5 | 0.5 | 0.5 | 0.5 | 0.5 |
| l-Befunolol.HCl | — | — | — | — | — | — |
| KH$_2$PO$_4$ (anhydrous) | 0.250 | 0.250 | 0.250 | 0.250 | 0.250 | 0.250 |
| Na$_2$HPO$_4$.12H$_2$O | 2.859 | 2.859 | 2.859 | 2.859 | 2.859 | 2.859 |
| Sodium chloride | 0.112 | 0.254 | 0.254 | 0.254 | 0.254 | 0.234 |
| Hydroxypropylmethyl cellulose | 0.5 | 0.5 | — | — | — | — |
| Polyvinyl alcohol | — | — | 1.5 | — | — | — |
| Methyl cellulose | — | — | — | 0.1 | — | — |
| Carboxymethyl cellulose | — | — | — | — | 0.02 | — |
| Hydroxyethyl cellulose | — | — | — | — | — | 0.1 |

TABLE 8-continued

|  |  |  |  |  |  |  |
|---|---|---|---|---|---|---|
| 10% Aqueous solution of benzalkonium chloride (ml.) | 0.8 | — | — | 0.01 | 0.1 | 0.3 |
| 10% Aqueous solution of benzethonium chloride (ml.) | — | 0.1 | 0.1 | — | — | — |
| Total volume (ml.) | 100 | 100 | 100 | 100 | 100 | 100 |
| pH | 7.4 | 7.4 | 7.4 | 7.4 | 7.4 | 7.4 |

|  | Ex. 15 | Ex. 16 | Ex. 17 | Ex. 18 | Ex. 19 | Ex. 20 |
|---|---|---|---|---|---|---|
| Components (g.) |  |  |  |  |  |  |
| dl-Befunolol.HCl | 0.5 | 0.5 | 0.5 | 0.5 | 2.0 | — |
| l-Befunolol.HCl | — | — | — | — | — | 0.25 |
| KH$_2$PO$_4$ (anhydrous) | 0.303 | 0.250 | 0.303 | 0.250 | 0.250 | 0.250 |
| Na$_2$HPO$_4$.12H$_2$O | 0.794 | 0.027 | 0.794 | 0.027 | 2.859 | 2.859 |
| Sodium chloride | 0.527 | 0.705 | 0.527 | 0.705 | — | 0.095 |
| Hydroxypropylmethyl cellulose | 0.5 | 0.5 | — | — | — | 0.5 |
| Polyvinyl alcohol | — | — | 1.5 | 1.5 | 1.5 | — |
| Methyl cellulose | — | — | — | — | — | — |
| Carboxymethyl cellulose | — | — | — | — | — | — |
| Hydroxyethyl cellulose | — | — | — | — | — | — |
| 10% Aqueous solution of benzalkonium chloride (ml.) | 0.1 | 0.1 | 0.1 | 0.1 | 0.8 | — |
| 10% Aqueous solution of benzethonium chloride (ml.) | — | — | — | — | — | 0.1 |
| Total volume (ml.) | 100 | 100 | 100 | 100 | 100 | 100 |
| pH | 6.7 | 5.4 | 6.7 | 5.4 | 7.4 | 7.4 |

|  | Ex. 21 | Ex. 22 | Ex. 23 | Ex. 24 | Ex. 25 | Ex. 26 |
|---|---|---|---|---|---|---|
| Components (g.) |  |  |  |  |  |  |
| dl-Befunolol.HCl | — | — | — | — | — | — |
| l-Befunolol.HCl | 0.25 | 0.25 | 0.25 | 0.25 | 0.25 | 0.25 |
| KH$_2$PO$_4$ (anhydrous) | 0.250 | 0.250 | 0.250 | 0.250 | 0.303 | 0.250 |
| Na$_2$HPO$_4$.12H$_2$O | 2.859 | 2.859 | 2.859 | 2.859 | 0.794 | 0.027 |
| Sodium chloride | 0.095 | 0.095 | 0.095 | 0.030 | 0.515 | 0.725 |
| Hydroxypropylmethyl cellulose | — | — | — | — | 0.5 | 0.5 |
| Polyvinyl alcohol | 1.5 | — | — | — | — | — |
| Methyl cellulose | — | 0.1 | — | — | — | — |
| Carboxymethyl cellulose | — | — | 0.02 | — | — | — |
| Hydroxyethyl cellulose | — | — | — | 0.1 | — | — |
| 10% Aqueous solution of benzalkonium chloride (ml.) | — | 0.1 | 0.1 | 0.3 | 0.1 | 0.1 |
| 10% Aqueous solution of benzethonium chloride (ml.) | 0.1 | — | — | — | — | — |
| Total volume (ml.) | 100 | 100 | 100 | 100 | 100 | 100 |
| pH | 7.4 | 7.4 | 7.4 | 7.4 | 6.7 | 5.4 |

What we claim is:

1. An ophthalmic solution for the decreasing of intraocular pressure comprising (A) 0.025 to 4.0 w/v % of an ophthalmologically acceptable, water-soluble salt of 2-acetyl-7-(2-hydroxy-3-isopropylaminopropoxy)bendzofuran, (B) 0.001 to 0.1 w/v % of benzalkonium chloride or benzethonium chloride, and (C) 0.01 to 2.0 w/v % of at least one member selected from the group consisting of polyvinyl alcohol, methyl cellulose, carboxymethyl cellulose, hydroxyethyl cellulose and hydroxypropylmethyl cellulose, the solution being adjusted to pH 5.0 to 8.0 with a buffer agent.

2. The ophthalmic solution of claim 1, wherein said 2-acetyl-7-(2-hydroxy-3-isopropylaminopropoxy)benzofuran is the dl-form.

3. The ophthalmic solution of claim 1, wherein the salt of dl-2-acetyl-7-(2-hydroxy-3-isopropylaminopropoxy)benzofuran is present in a concentration of 0.05 to 4.0 w/v %.

4. The ophthalmic solution of claim 1, wherein the salt of dl-2-acetyl-7-(2-hydroxy-3-isopropylaminopropoxy)benzofuran is present in a concentration of 0.1 to 2.0 w/v %.

5. The ophthalmic solution of claim 1, wherein said 2-acetyl-7-(2-hydroxy-3-isopropylaminopropoxy)benzofuran is the l-form.

6. The ophthalmic solution of claim 1, wherein the salt of l-2-acetyl-7-(2-hydroxy-3-isopropylaminopropoxy)benzofuran is present in a concentration of 0.025 to 2.0 w/v %.

7. The ophthalmic solution of claim 1, wherein the salt of l-2-acetyl-7-(2-hydroxy-3-isopropylaminopropoxy)benzofuran is present in a concentration of 0.05 to 1.0 w/v %.

8. The ophthalmic solution of claim 1, wherein the concentration of the component (B) is from 0.003 to 0.01 w/v %.

9. The ophthalmic solution of claim 1, wherein the pH of the solution is from 6.8 to 7.6.

10. The ophthalmic solution of claim 1, wherein said ophthalmologically acceptable, water-soluble salt of 2-acetyl-7-(2-hydroxy-3-isopropylaminopropoxy)benzofuran is the hydrochloric acid salt.

11. The ophthalmic solution of claim 1, wherein (C) is selected from the group consisting of polyvinyl alcohol and hydroxypropylmethylcellulose.

* * * * *